United States Patent [19]
Wrobel

[11] Patent Number: 4,946,858
[45] Date of Patent: Aug. 7, 1990

[54] NOVEL SPIROSUCCINIMIDES AS ALDOSE REDUCTASE INHIBITORS AND ANTIHYPERGLYCEMIC AGENTS

[75] Inventor: Jay E. Wrobel, Lawrenceville, N.J.

[73] Assignee: American Home Products Corporation, New York, N.Y.

[21] Appl. No.: 373,016

[22] Filed: Jun. 28, 1989

Related U.S. Application Data

[62] Division of Ser. No. 260,149, Oct. 20, 1988, Pat. No. 4,900,739.

[51] Int. Cl.$^5$ .................. C07D 487/10; A61K 31/40
[52] U.S. Cl. ..................................... 514/409; 548/410
[58] Field of Search ...................... 548/410; 514/409

[56] References Cited

U.S. PATENT DOCUMENTS 4,720,449  1/1988  Borror ........................ 430/338

FOREIGN PATENT DOCUMENTS 168181  1/1980  European Pat. Off. ............ 548/183
65407  11/1982  European Pat. Off. .
147805  4/1985  European Pat. Off. .
136143  7/1985  European Pat. Off. .

Primary Examiner—Robert Gerstl
Attorney, Agent, or Firm—Walter Patton

[57] ABSTRACT

This invention relates to novel spirosuccinimide derivatives, to the processes for their preparation, to methods for using the compounds, and to pharmaceutical preparations thereof. The compounds have pharmaceutical properties which render them beneficial for the treatment of diabetes mellitus and associated conditions.

13 Claims, No Drawings

SPIROSUCCINIMIDES AS ALDOSE REDUCTASE INHIBITORS AND ANTIHYPERGLYCEMIC AGENTS

This is a divisional of co-pending application Ser. No. 260,149 filed on Oct. 20, 1988 now U.S. Pat. No. 4,900,739.

BACKGROUND OF THE INVENTION

This invention relates to novel spirosuccinimide derivatives, to the processes for their preparation, to methods for using the compounds, and to pharmaceutical preparations thereof. The compounds have pharmaceutical properties which render them beneficial for the treatment of diabetes mellitus and associated conditions.

For many years diabetes mellitus has been treated with two established types of drugs, namely insulin and oral hypoglycemic agents. These drugs have benefited hundreds of thousands of diabetics by improving their well-being and prolonging their lives. However, the resulting longevity of diabetic patients has led to complications such as neuropathy, nephropathy, retinopathy, cataracts and atherosclerosis. These complications have been linked to the undesirable accumulation of sorbitol in diabetic tissue, which in turn resulted from the high levels of glucose characteristic of the diabetic patient.

In mammals, including humans, the key enzyme involved in the conversion of hexoses to polyols (e.g. the sorbitol pathway) is aldose reductase. J. H. Kinoshita and collaborators, see J. H. Kinoshita et al, Biochem, Biophys. Acta, 158,472 (1968) and references cited therein, have demonstrated that aldose reductase plays a central role in the etiology of galactosemic cataracts by effecting the conversion of galactose to dulcitol (galactitol) and that an agent capable of inhibiting aldos reductase can prevent the detrimental accumulation of dulcitol in the lens. Furthermore, a relationship between elevated levels of glucose and an undesireable accumulation of sorbitol has been demonstrated in the lens, peripheral nerves and kidney of diabetic animals, see A. Pirie and R. van Heyningen, Exp. Eye Res., 3,124 (1964); L. T. Chylack and J. H. Kinoshita, Invest. Ophthal., 8,401 (1969) and J. D. Ward and R. W. R. Baker, Diabetol., 6,531 (1970).

The closest prior art is D.R. Brittain, European Patent 168181 (1985) and D. R. Brittain et al, European Patent 65407 (1982). D. R. Brittain et al disclose spirosuccinimide-indolinone derivatives having aldose reductase activity. Still other related compounds having similar activity are spirosuccinimide derivatives of T. Irikura, et al, European Patent 147805 (1984) and C. A. Lipinsik, European Patent 136143, (1984). The compounds of the present invention differ in that they are members of novel ring systems. Accordingly, the present compounds represent an important new approach for treatment of diabetes mellitus.

Non-insulin dependent diabetes mellitus (Type II diabetes) is usually treated by a regimen including diet, exercise, oral agents such as sulfonylureas and, in more severe cases, insulin. Many of these hypoglycemic agents exhibit severe side effects. This, along with their generally limited efficacy, has created a need for new, novel and more potent antidiabetic agents which do not possess these drawbacks.

Ciglitazone [(±)-5-[4-[(1-methylcyclohexyl)methoxy]benzyl]-thiazolidine-2,4-dione] is currently considered one of the most unique and promising drugs for treatment of hyperglycemia and hyperinsulinemia [Fujita et al, Diabetes, 32, 804 (1983)] because it normalizes these parameters. K. Megura et al, European Patent 208420 (1986), K. Megura et al, European Patent 193256 (1985), disclose other thiazolinine-dione containing compounds having antihyperglycemic activity useful for treating diabetes. The compounds of the present invention also possess antihyperglycemic activity and are of novel structure. Accordingly, the present compounds represent an important new approach for the treatment of diabetes mellitus.

SUMMARY OF THE INVENTION

The novel spirosuccinimides of this invention are represented by formula (I)

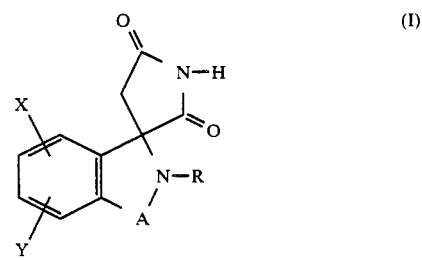

(I)

wherein A is $SO_2$ or CO; R is lower alkyl containing 1 to 6 carbon atoms, benzyl, halogen substituted benzyl, (2-naphthalenyl)methyl, (1-bromo-2-naphthalenyl)methyl; X is hydrogen, halogen, lower alkyl containing 1 to 4 carbon atoms, lower alkoxy containing 1 to 4 carbon atoms, lower alkylthio containing 1 to 4 carbon atoms, carboalkoxy containing 1 to 4 carbon atoms, phenyl, nitro; Y is hydrogen or chlorine; or X and Y are joined to form CH=CH—CH=CH, and the pharmaceutically acceptable salts thereof.

More specifically the compounds of formula (I) can be divided into two subgenera, one for A is $SO_2$ and one for A is CO. When A is $SO_2$, the compounds of formula (I) are derviatives of spiro[1,2-benzisothiazole-3(2H),3'-pyrolidine]-2',5'-dione 1,1-dioxide and are represented by formula (II) and are numbered as follows:

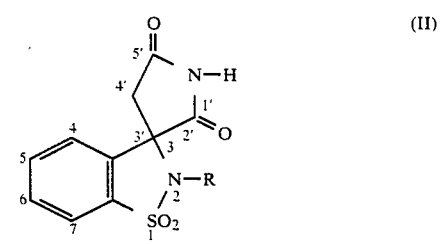

(II)

wherein R is lower alkyl containing 1 to 4 carbon atoms, benzyl, halogen substituted benzyl, (2-naphthalenyl)methyl, (1-bromo-2-naphthalenyl)methyl, and the pharmaceutically acceptable salts thereof.

When A is CO, the compounds of formula (I) are derivatives of spiro[1H-isoindole-1,3'-pyrrolidine]-2',3,5'(2H)-trione and are represented by formula (III) and are numbered as follows:

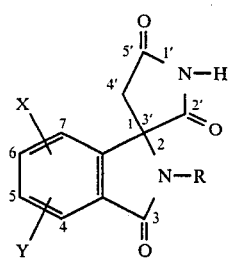 (III)

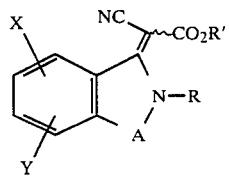 (IV)

wherein R is lower alkyl containing 1 to 4 carbon atoms, benzyl, halogen substituted benzyl; X is hydrogen, lower alkyl containing 1 to 4 carbon atoms, lower alkoxy containing 1 to 4 carbon atoms, lower alkylthio containing 1 to 4 carbon atoms, carboalkoxy containing 1 to 4 carbon atoms, phenyl, nitro; Y is hydrogen or chlorine; or X and Y are joined to form CH=CH—CH=CH, and the pharmaceutically acceptable salts thereof.

The preferred compounds of the present invention are represented by formula (II) wherein R is halogen substituted benzyl or are represented by formula (III) wherein R is halogen substituted benzyl, X and Y are hydrogen; or R is lower alkyl containing 1 to 2 carbon atoms, Y is hydrogen and X is halogen or lower alkyl containing 1 to 3 carbon atoms or 5 -phenyl; or R is lower alkyl consisting of 1 to 2 carbons, X is 5-Cl and Y is 6-Cl; or R is lower alkyl containing 1 to 2 carbon atoms, X and Y are joined to form 5, 6—CH=CH—CH=CH, and the pharmaceutically acceptable salts thereof.

The most preferred compounds of the present invention are designated:

6-chloro-2-methylspiro[1H-isoindole-1,3'-pyrrolidine]-2',3,5'(2H)-trione;

5,6-dichloro-2-methylspiro[1H-isoindole-1,3'-pyrrolidine]-2',3,5'(2H)-trione;

5-chloro-2-methylspiro[1H-isoindole-1,3'-pyrrolidine]-2',3,5'(2H)-trione;

2,4-dimethylspiro[1H-isoindole-1,3'-pyrrolidine]-2',3,5'(2H)-trione;

2-methylspiro[1H-benz[f]isoindole-1,3'-pyrrolidine]-2',3,5'(2H)-trione;

2-[(4-bromo-2-fluorophenyl)methyl]-2,3-dihydrospiro[1,2-benzisothiazole-3,3'-pyrrolidine]-2',5'-dione 1,1-dioxide;

2-[(4-bromophenyl)methyl]-2,3-dihydrospiro[1,2-benzisothiazole-3,3'-pyrrol-idine]-2',5'-dione 1,1-dioxide;

2-[(4-bromo-2-fluorophenyl)methyl]spiro[1H-isoindole-1,3'pyrrolidine]-2',3,5'(2H)-trione;

and the pharmaceutically acceptable salts thereof.

The compounds of formula (I) all posses at least one asymmetric carbon atom, namely the spiro carbon atom at position 3' of the pyrrolidine ring. The compounds of formula (I) therefore exist, and may be isolated, in one or more racemic and optically active forms. This invention encompasses the compounds of formula (I) in racemic form or in any optically-active form.

Also included in the present invention are the chemical intermediate compounds of formula (IV)

wherein A, R, X, and Y are as defined above, and R' is lower alkyl containing 1 to 3 carbon atoms. The compounds of formula (IV) are usually a mixture of geometric isomers and are generally used without purification in the next step. The variable bond (~) in formula (IV) represents a mixture of geometric isomers.

The novel spirosuccinimides of this invention can be prepared by the processes described hereinafter.

A method is provided for preventing or relieving diabetes mellitus associated complications in a diabetic mammal by administering to said mammal a prophylactic or alleviating amount of a compound of formula (I). Such complications include neuropathy, nephropathy, retinopathy, keratopathy, diabetic uveitis, and cataracts.

A method is provided for preventing or relieving diabetes mellitus associated hyperglycemia in a diabetic mammal by administering to said mammal a prophylactic or alleviating amount of a compound of formula (I).

The compounds of the present invention may also be used as antihyperlipidemic or antihyperinsulinemic agents.

The compounds of formula (I), when admixed with a pharmaceutically acceptable carrier, form a pharmaceutical composition which can be used according to the preceding method.

DETAILED DESCRIPTION OF THE INVENTION

The compounds of formula (I) form salts with suitable therapeutically acceptable inorganic and organic bases. These derived salts possess the same activity as their parent acid and are included within the scope of this invention. The acid is transormed in excellent yield into the corresponding therapeutically acceptable salt by neutralization of said acid with the appropriate inorganic or organic base. The salts are administered usually in the same manner as the parent acid compounds. Suitable inorganic bases to form these salts include, for example, the hydroxides, carbonates or bicarbonates of the therapeutically acceptable alkali metals or alkaline earth metals, for example, sodium, potassium, magnesium, calcium and the like. Suitable organic basis include the following amines: benzylamine; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di- and trialkanolamines, the alkanol radicals of which contain up to three carbon atoms, for example, mono-, di- and triethanolamine; alkylene-diamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalky derivatives, such as N-methylmorpholine and N-(2-hydroxyethyl)piperidine, as well as pyridine. Furthermore, there may be mentioned the corresponding quaternary salts, such as the tetraalkyl (for example tetramethyl), alkyl-alkanol (for example methyl-triethanol and trimethyl-monoethanol) and cyclic ammonium salts, for example the N-methylpyridinium, N-methyl-N-(2-hydroxyethyl)morpholinium, N,N-dimethylmorpholinium, N-methyl-N-(2-hydroxyethyl)morpholinium. N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula (I) in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acidic compound of formula (I) is dissolved in a suitable solvent of either moderate or low polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of lower polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula (I) with an equivalent amount of the corresponding quaternary ammonium hydroxide in water solution, followed by evaporation of the water.

The novel spirosuccinimides of this invention may be administered to mammals, for example, man, monkeys or dogs, either alone or in dosage forms, i.e., capsules or tablets, combined with pharmacologically acceptable excipients.

Advantageously the compounds of this invention may be given orally. However, the method of administering the present active ingredients of this invention is not to be construed as limited to a particular mode of administration. For example, the compounds may be administered topically directly to the eye in the form of drops of sterile, buffered ophthalmic solutions, preferably of pH 7.2–7.6. Also, they may be administered orally in solid form containing such excipients as starch, milk sugar, certain types of clay and so forth. They may also be administered orally in the form of solutions or they may be injected parenterally. For parenteral administration they may be used in the form of a sterile solution, preferably of pH 7.2–7.6, containing a pharmaceutically acceptable buffer.

The dosage of the spirosuccinimides will vary with the form of administration. Furthermore, it will vary with the particular host under treatment. Generally, treatment is initiated small dosages substantially less than the optimal dose of the compound. In general, the compounds of this invention are most desirably administered at a concentration level that will generally afford effective results without causing any harmful of deleterious side effects. For topical administration, a 0.05–1.8% solution may be administered dropwise in the eye. The frequency of instillation varies with the subject under treatment from a drop every two or three days to once daily. For oral or parenteral administration a preferred level of dosage ranges from about 0.5 mg to about 1000 mg per kilo of body weight per day, although aforementioned variations will occur. However, a dosage level that is in the range of from about 5.0 mg to about 60 mg per kilo of body weight per day is most satisfactory.

Unit dosage forms such as capsules, tablets, pills and the like may contain from about 25 mg to about 1250 mg of the active ingredients of this invention with a pharmaceutical carrier. Thus, for oral administration, capsules can contain from between about 25 mg to about 1250 mg of the active ingredients of this invention with or without a pharmaceutical diluent. Tablets, either effervescent or noneffervescent, can contain between about 25 to 1250 mg of the active ingredients of this invention together with conventional pharmaceutical carriers. Thus, tablets which may be coated and either effervescent or noneffervescent, may be prepared according to the known art. Inert diluents or carriers, for example, magnesium carbonate or lactose, can be used together with conventional disintegrating agents for example, magnesium stearate.

The aldose reductase inhibiting effects of the compounds of formula (I) were tested by employing an in vitro testing procedure similar to that described by S. Hayman and J. H. Kinoshita, J. Biol. Chem., 240, 877 (1965). In the present case the procedure of Hayman and Kinoshita was modified in that the final chromatography step was omitted in the preparation of the enzyme from bovine lens. The results are tabulated in Table I.

TABLE 1

| Compound of | % Inhibition in Vitro | |
|---|---|---|
| | $10^{-5}$M | $10^{-6}$M |
| Example 101 | 40 | 6 |
| Example 102 | 91 | 80 |
| Example 103 | 45 | 5 |
| Example 104 | 52 | 3 |
| Example 105 | 63 | 16 |
| Example 112 | 59 | 25 |
| Example 113 | 57 | 20 |
| Example 115 | 82 | 45 |
| Example 116 | 84 | 54 |
| Example 117 | 86 | 45 |
| Example 120 | 88 | 72 |
| Example 121 | 85 | 70 |
| Example 122 | 94 | 83 |
| Example 123 | 93 | 74 |
| Example 124 | 95 | 82 |
| Example 125 | 88 | 57 |
| Example 126 | 85 | 65 |
| Example 127 | 92 | 71 |
| Example 128 | 78 | 37 |
| Example 129 | 83 | 56 |
| Example 130 | 87 | 60 |
| Example 131 | 49 | 12 |
| Example 132 | 91 | 77 |
| Example 133 | 89 | 61 |
| Example 134 | 87 | 49 |
| Example 135 | 84 | 59 |
| Example 136 | 90 | 81 |
| Sorbinil (reference standard, note 1) | 83 | 45 |

TABLE 1-continued

| Compound of | % Inhibition in Vitro | |
|---|---|---|
| | $10^{-5}M$ | $10^{-6}M$ |
| Tolrestat (reference standard, note 2) | 98 | 94 |

Notes
(1) Sorbinil [(4S)-2,3-dihydro-6-fluorospiro[4H-1-benzopyran-4,4'-imidazoli-dine]-2',5'-dione]
(2) Tolrestat N-[(6-methoxy-5-(trifluoromethyl)-1-naphthalenyl]thioxomethyl]-N-methylglycine The aldose reductase inhibiting property of the compounds of this invention and the utilization of the compounds in preventing, diminishing and alleviating diabetic complications by lowering polyol accumulation were also demonstrable in experiments using galactosemic rats, see Dvornik et al, Science, 182, 1146 (1973). Such experiments are exemplified hereinbelow after the listing of the following general comments pertaining to these experiments:

(a) Four or more groups of six male rats, 50–70 g, Sprague-Dawley strain, were used. The first group, the control group, was fed a mixture of laboratory chow (rodent Laboratory Chow, Purina) and glucose at 20% (w/w %) concentration. The untreated galactosemic group and the drug-treated groups were fed a similar diet in which galactose is substituted for glucose. The test compound was either admixed to the diet or administered by gavage. In experiments involving compound administration in the diet, the average dose administered was calculated from the actual food intake of the animals in each group. The concentration of galactose in the diet of the treated groups was the same as that for the untreated galactosemic groups.

(b) After four days, the animals were killed by decapitation. The eyeballs were removed and punctured with a razor blade; the freed lenses were rolled gently on filter paper and weighed. The sciatic nerves were dissected as completely as possible and weighed. Both tissues when frozen can be kept up to two weeks before being analyzed for galactitol.

(c) The polyol determination was performed by a modification of the procedure of M. Kraml and L. Cosyns, Clin. Biochem., 2, 373 (1969). Only two minor reagent changes were made: (a) the rinsing mixture was an aqueous 5% (w/v) trichloroacetic acid solution and (b) the stock solution was prepared by dissolving 25 mg of dulcitol in 100 mL of an aqueous trichloroacetic acid solution. [N.B.: For each experiment the average value found in the tissue from rats fed the glucose diet was subtracted from the individual values found in the corresponding tissue in galactose-fed rats to obtain the amount of polyol accumulated.]

The tabulated results in Table 2 show that the spirosuccinimides of this invention show the property that they diminish the accumulation of galactitol in the lenses and sciatic nerves of rats fed galactose. The figures under L, N, and D represent the percentage decrease of galactitol accumulation in the tissues of the lens, sciatic nerve, and diaphragm, respectively, for treated rats as compared to untreated rats.

Examination of the results tabulated in Table 2 below shows that the spirosuccinimides of this invention are well suited as aldose reductase inhibitors and they lower accumulation of sorbitol or galactitiol in the diabetic or galactosemic rats. For example, 6-chloro-2-methyl-spiro[1H-isoindole-1,3'-pyrrolidine]-2',3,5'(2H)-trione, the compound of Example 102, at a dose of 3 mg/kg/day comparable results to sorbinil at 4 mg/kg/day and tolrestat at 3 mg/kg/day in the sciatic nerve.

TABLE 2

| Compound of | % Lowering of dulcitol accumulation In Vivo | | | |
|---|---|---|---|---|
| | mg/kg | % L | % N | % D |
| Example 102 | 25 | 51 | 84 | 81 |
| | 3 | 9 | 38 | 43 |
| Example 104 | 104 | 13 | NS | NS |
| Example 116 | 101 | NS | NS | 30 |
| Example 120 | 81 | 54 | 77 | 80 |
| | 3 | NS | 21 | NS |
| Example 122 | 50 | 71 | 94 | 90 |
| | 3 | NS | 20 | 25 |
| Example 124 | 10 | 14 | 47 | 59 |
| Example 125 | 10 | 13 | 32 | 47 |
| | 6 | 7 | 21 | 37 |
| | 3 | NS | NS | 23 |
| Example 135 | 10 | 29 | 63 | 69 |
| | 6 | NS | 50 | 57 |
| | 3 | NS | NS | 37 |
| Example 136 | 9 | 6 | 34 | 55 |
| | 6 | 13 | 27 | 43 |
| | 3 | NS | NS | 29 |
| Sorbinil (reference standard) | 4 | 46 | 55 | 69 |
| Tolrestat (reference standard) | 3 | NS | 30 | 80 |

NS = not significant
L = lens
N = nerve
D = diaphragm

The blood glucose lowering activity of the compounds of this invention were demonstrable in experiments using diabetic (db/db) mice.

The db/db (C57BL/KsJ) mouse exhibits many metabolic abnormalities that are associated with non-insulin dependent diabetes mellitus (Type II) in humans. The animals are obese, glucose intolerant and have fasting hyperglycemia which is sometimes accompanied by a paradoxical hyperinsulinemia. Furthermore, the db/db mouse will eventually develop some of the long-term complications that have been associated with diabetes mellitus. [See Coleman Diabetes, 31 (Suppl. 1), 1 (1982)]. In spite of these commonalities, the acute administration of sulfonylureas (even at extremely high dosages) will not reduce the hyperglycemia of the db/db mouse. [See Tutwiler et al, Diabetes 27, 856 (1978)]. The ability of a few other hypoglycemic agents to be effecive in this species suggest that the other agents have mechanisms of action which are different from that of the sulfonylureas [ibid; Lee et al, Diabetes 31:12 (1982); Chang et al, Diabetes 32, 830 (1983); Hosokawa et al, Diabetes 34, 267 (1985)]. Such compounds, therefore, are more likely to be efficacious in the population of Type II diabetic patients that do not respond to sulfonylurea therapy. The experiments are exemplified hereinbelow after the listing of the following general procedure pertaining to these experiments.

On the morning of Day 1, 35 mice [male db/db (C57BL/KsJ), Jackson Laboratories, 2 to 7 months of age and body weight 35 to 60 g] were fasted for 4 hours, weighted and a baseline blood sample was collected from the tail-tip of each mouse without anesthesia, placed directly into a fluoride-containing tube, mixed and maintained on ice. Food was then returned to the mice. The plasma was separated and levels of glucose in plasma determined by the Abbott VP Analyzer. Because of the variable plasma glucose levels of the db/db mice, 5 mice having the most extreme (i.e., highest or lowest) plasma glucose levels were excluded and the remaining 30 mice were randomly assigned into 7 groups of equivalent means plasma glucose levels:

| Group A: Vehicle control | N = 6 |
| --- | --- |
| Group B: Positive control (ciglitazone) | N = 4 |
| Group C: 1st Test drug | N = 4 |
| Group D: 2nd Test drug | N = 4 |
| Group E: 3rd Test drug | N = 4 |
| Group F: 4th Test drug | N = 4 |
| Group H: 5th Test drug | N = 4 |

On the afternoon of Days 1, 2 and 3 the vehicle, control or test drugs were administered (p.o.) to the ad libitum fed mice. The positive control, ciglitazone [(±)-5-[4-[(1-methylcyclohexy]methoxy]benzyl]-thiazolidine-2,4-dione] see Fujita et al, Diabetes, 32, 804 (1983), was given by gavage at a dose of 100 mg/kg/day. The test compounds were given by gavage at a dose of 100 mg/kg/day unless otherwise noted in Table 3.

On the morning of Day 4, the mice were weighted and fasted, but water was available ad libitum. Three hours later, a blood sample was collected and then the mice were given the fourth administration of drug or vehicle. Blood samples were collected again from the unanesthetized mice at 2 and 4 hours after drug administration. The plasma was separated and levels of glucose in plasma determined by the Abbott VP Analyzer.

For each mouse, the percent change of it's plasma glucose level on Day 4 (mean of the 2 and 4 hour samples) from it's respective level before drug administration (Day 1 baseline sample) was determined as follows:

$$\frac{\text{Mean of 2 and 4 hour Samples (Day 4)}}{\text{Baseline Sample (Day 1)}} \times 100$$

Analysis of variance followed by Dunnett's multiple comparison (one-sided) was used to estimate the degree of statistical significance of the difference between the vehicle group and the individual drug-treated groups. A drug was considered active, at the specific dosage administered, if the difference of the plasma glucose level has a $p < 0.05$.

The tabulated results in Table 3 show that the spirosuccinimides of this invention show the property that they lower blood glucose levels in the postprandial diabetic (db/db) mice. The actual difference between the mean percent change of the vehicle and the drug-treated group is reported in Table 3.

Examination of the results tabulated in Table 3 below shows that the spirosuccinimides of this invention are well suited as antihyperglycemic agents for they lower blood glucose levels in diabetic mice. For example, 2-[(4-bromo-2-fluorophenyl)methyl]-2,3-dihydrospiro[1,2-benzisothiazole-3,3'-pyrrolidine]-2',5'-dione 1,1-dioxide, the compound of Example 104, at a dose of 100 mg/kg gives comparable results to ciglitazone at 100 mg/kg.

TABLE 3

| Compound of | Dose mg/kg | % Change from vehicle |
| --- | --- | --- |
| Example 102 | 100 | NS |
| Example 104 | 100 | −48 |
|  | 20 | NS |
| Example 105 | 100 | −27 |
| Example 106 | 100 | −37 |
| Example 110 | 100 | −17 |
| Example 111 | 87 | −27 |
| Example 114 | 100 | −22 |
| Example 115 | 100 | −21 |
| Example 116 | 100 | −36 |
| Example 120 | 100 | NS |
| Example 122 | 100 | −31 |
| Example 124 | 100 | NS |
| Ciglitazone (reference standard) | 100 | −33 |

NS = not significant

The Process

The spirosuccinimides of this invention can be prepared by the following reaction schemes:

Scheme 1

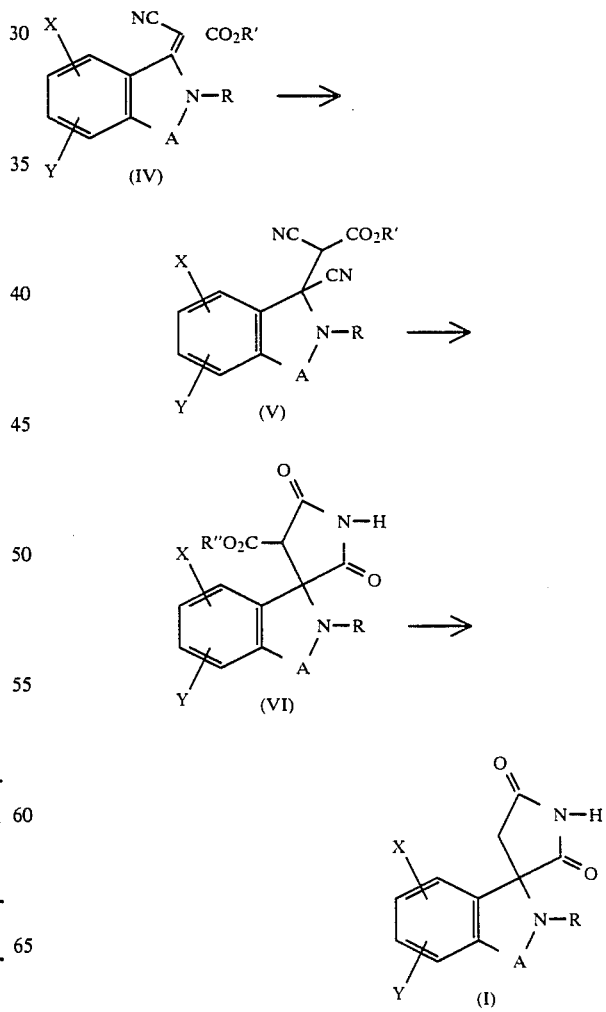

Scheme 2
Preparation of (IV) (A is SO₂)
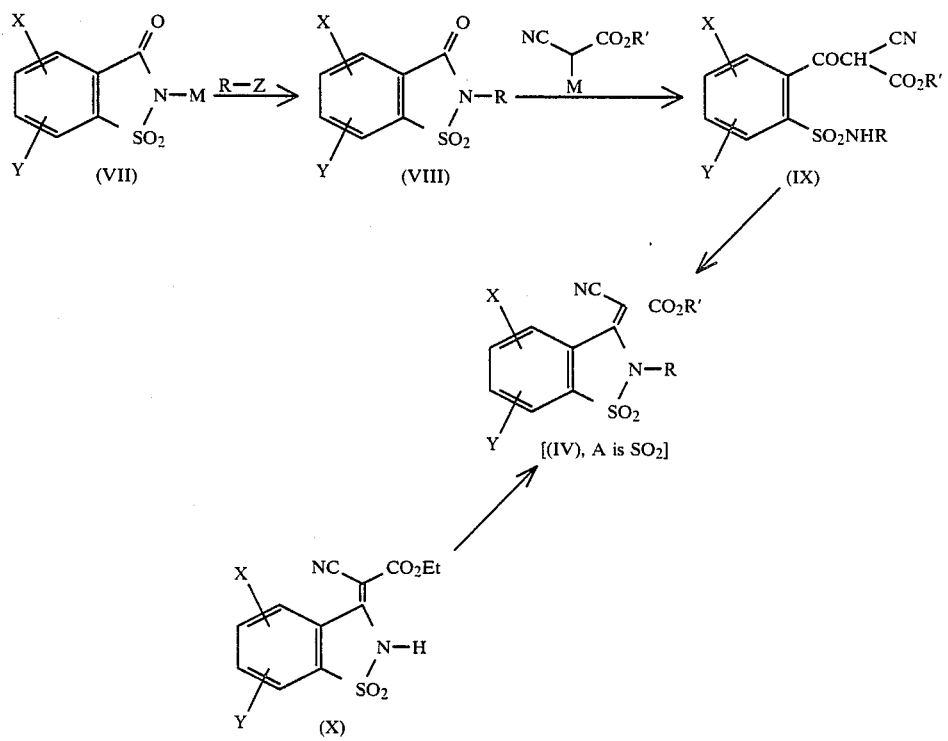
Scheme 3
Preparation of (IV) (A is CO)
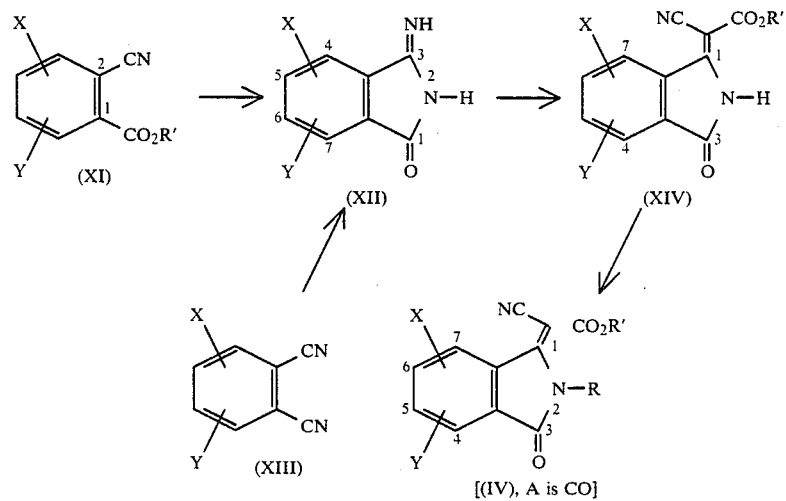
Scheme 4
Preparation of (XI)
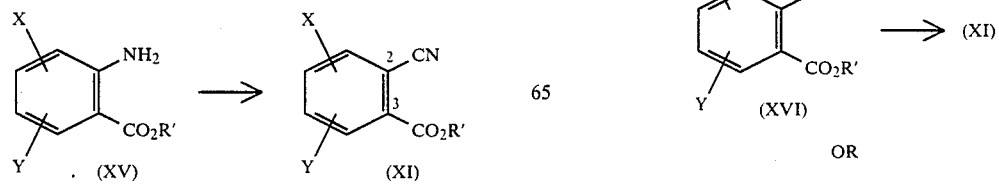

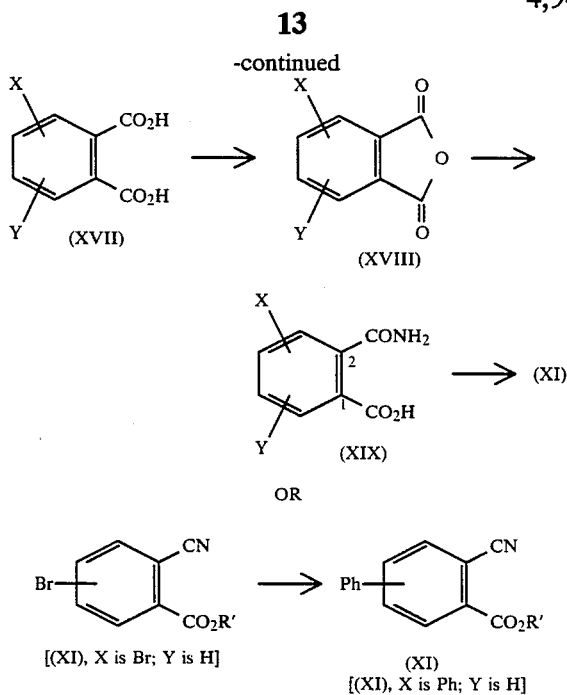

wherein A, R, X and Y are as defined above and R' is lower alkyl; R" is hydrogen or lower alkyl; M is H, Li, Na, K; and Z is a halogen (Cl, Br or I).

Referring to Scheme 1, the unsaturated cyanoester of formula (IV), wherein R' is a lower alky group containing 1 to 3 carbon atoms or a geometric isomer thereof, is reacted with ametal cyanide salt (1 to 2 equivalents) such as sodium cyanide or potassium cyanide in an alcoholic solvent such as methanol or ethanol or in a polar aprotic solvent such as DMSO at a temperature range of 10° to 50° C. to afford the dinitrile ester of formula (V), wherein R' is a lower alkyl group. The compound of formula (V) is usually a mixture of diasteriomeric products and is either, not isolated, but allowed to cyclize in situ, or is not purified, but used as such in the next step.

The compound of formula (V) is cyclized employing an inorganic acid catalyst such as hydrogen halide, sulfuric acid or polyphosphoric acid in an alcoholic solvent such as methanol or ethanol at a temperature range of 0° to 120° C. to afford the compound of formula (VI), wherein R" is hydrogen or lower alkyl containing 1 to 3 carbon atoms. The compounds of formula (VI) are usually a mixture of diasteriomeric products and are generally not purified but used as is in the next step.

The compound of formula (VI), wherein R" is hydrogen is decarboxylated to afford the compound of formula (I) upon heating in the temperature range of 50° to 250° C. in a suitable solvent such as acetic acid. The acid of formula (VI), wherein R" is hydrogen, is conveniently obtained from an acid ester of formula (VI) wherein R" is lower alkyl, by base hydrolysis employing aqueous sodium or potassium hydroxide in a suitable solvent such as methanol at a temperature range of 0° to 60° C. The acid is generated from the salt obtained by acidification with a mineral acid.

The ester of formula (VI), wherein R" is lower alkyl can be directly converted to the compound of formula (I) without isolation of the acid of formula (VI), wherein R" is hydrogen. That is, convenient conditions for the formation and subsequent decarboxylation of (VI), wherein R" is hydrogen are provided by heating the ester of formula (VI), wherein R" is lower alkyl in an alkanoic acid such as acetic acid, alone or in the presence of an inorganic acid such as hydrochloric acid at a temperature range of 100° to 130° C.

The compounds of formula (IV), wherein A is $SO_2$, are prepared according to the process referred to in Scheme 2.

The metallated saccharin derivative of formula (VII), wherein M is Li, Na or K is treated with the appropriate alkylating agent R-Z, wherein Z is halogen (Cl, Br or I) to afford the alkylated saccharin derivative of formula (VIII). The reaction is performed in a polar aprotic solvent such as DMF or DMSO at a temperature range of 80° to 120° C. The metallated saccharin derivative of formula (VII), wherein M is Li, Na or K is obtained commercially or can be generated from the saccharin derivative, wherein M is H, by reaction with the appropriate alkali metal base such as potassium carbonate or sodium hydroxide. The compound of formula (VII), wherein M is Li, Na or K can be isolated or generated in situ.

The saccharin derivative of formula (VIII) is then reacted with a metal salt of a lower alkyl ester of cyanoacetic acid (1 to 3 equivalents) to afford the ring opened product (IX) wherein R' is lower alkyl. The reaction is conveniently carried out in a suitable solvent such as THF at a temperature range of 20° to 100° C. The metal salt of the lower alkyl ester of cyanoacetic acid is conveniently generated in situ from the appropriate lower alkyl ester of cyanoacetic acid and a base such as potassium t-butoxide or sodium hydride at a temperature range of 20° to 100° C.

The compound of formula (IX) is then cyclized with loss of water to afford the compound of formula [(IV) A is $SO_2$]. This cyclization is conveniently performed with a suitable dehydrating agent such as acetic ahhydride or trifluoroacetic anhydride at a temperature range 50° to 120° C. or by using a mixture of an amine base (1 to 3 equivalents) such as triethylamine or pyridine with actic anhydride at a temperature range of 0° to 50° C. The compounds of formula (IV) (A is $SO_2$) are usually a mixture of geometric isomers and are generally not purified but used as is in the next step.

Alternatively the compound of formula [(IV) A is $SO_2$, X and Y are H, R' is $CH_2CH_3$] can be prepared from the know compound of formula (X) [C. Melchiorre et al, Ann Chim (Rome) 61, 399 (1971)]. The compound of formula (X) is first reacted with a base such as potassium carbonate or sodium hydride and the resulting salt is reacted with a suitable alkylating agent (1 to 3 equivalants) in a polar aprotic solvent such as DMF or DMSO at 80° to 160° C.

The compounds of formula (IV), wherein A is CO, are prepared according to the process referred to in Scheme 3.

The cyanoester of formula (XI), wherein R' is lower alkyl is reacted wtih ammonia gas in an alcoholic solvent such as methanol to afford the compound of formula (XII). The reaction is conveniently performed at a temperature range of 0° to 60° C. over a 1 to 3 day period.

Alternatively the compound of formula (XII) can be prepared by reaction of the dinitrile of formula (XIII) with an inorganic acid such as hydrogen halide or sulfuric acid in an alcoholic solvent such as isopropanol or 2-butanol at a temperature of 20° to 60° C.

The compound of formula (XII) is then reacted with a lower alkyl ester of cyanoacetic acid (1 to 10 equivalents) to afford the compound of formula (XIV), wherein R' is lower alkyl. The reaction is conveniently performed at a temperature range of 150° to 220° C.

The compound of formula (XIV) is then alkylated with a suitable alkylating agent to afford the compound of formula [(IV) A is CO]. The reaction is conveniently performed by first reacting the compound of formula (XIV) with a base such as potassium carbonate or sodium hydride to form the metal salt of the compound of formula (XIV). This salt is then reacted with the appropriate alkyl or substituted benzyl halide (1 to 3 equivalents) to afford the compound of formula (IV). This reaction is performed in a polar aprotic solvent such as DMF or DMSO at a temperature range of 80° to 120° C. The compounds of formula [(IV) A is CO] are usually a mixture of geometric isomers and are generally not purified, but used as is in the next step.

The compounds of formula (XI) are prepared by the processes referred to in Scheme 4.

The amino ester of formula (XV), wherein R' is lower alkyl is reacted with sodium nitrite (1 equivalent) and an inorganic aqueous acid such as hydrohalic, sulfuric or phosphoric acid at a temperature range of 0° to 15° C. to afford the corresponding diazonium salt

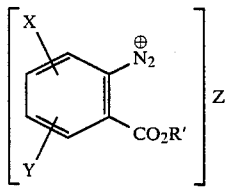

wherein Z is an anion such as halide, sulfate or phosphate. The diazonium salt is not isolated but immediately reacted with copper (I) cyanide (1 to 5 equivalents) at a temperature range of 50° to 100° C. to afford the nitrile ester of formula (XI). The copper (I) cyanide used in this reaction is a commercial reagent or is generated in situ from the reaction of potassium cyanide with copper (II) sulfate.

Alternatively the compound of formula (XVI), wherein Z is halogen, is also used to prepare the compound of formula (XI). The reaction is conveniently performed by reacting the compound of formula (XVI) with copper (I) cyanide (1 to 5 equivalents) in a polar aprotic solvent such as DMF or 1-methyl-2-pyrrolidinone at a temperature range of 150° to 220° C.

Still alternatively, the compound of formula (XI) can be prepared from the dicarboxylic acid of formula (XVII) by a three step process. The dicarboxylic acid of formula (XVII) is converted to its anhydride form of formula (XVIII) by conventional methods such as heating the compound of formula (XVII) in acetic anhydride at a temperature range of 100° to 150° C. The anhydride of formula (XVII) is then reacted with ammonia gas that has been dissolved in a suitable solvent such as water of THF. The reaction is conveniently performed at a temperature range of 0° to 25° C. The product isolated from the reaction is the ammonium salt of the acid of formula (XIX). The acid of formula (XIX) is then obtained by acidification of the ammonium salt with an aqueous inorganic acid such as hydrohalic, sulfuric or phosphoric acid.

The amide acid of formula (XIX) was then reacted with a lower alkyl chloroformate such as methyl chloroformate and an amine base such as triethylamine to afford the compound of formula (XI). This combination of reagents causes dehydration of the amide function of (XIX) to a nitrile function with concomitant esterification of the acid function. The reaction is conveniently performed in an inert solvent such as dichloromethane at a temperature range of 0° to 30° C.

Alternatively, the compound of formula (XI) wherein X is phenyl, Y is H can be prepared from the compound of formula (XI), wherein X is Br, Y is H utilizing the procedure of N. Miyaura et al, Syn Comm. 11 (7), 513 (1981). The compound of formula (XI), X is Br, Y is H is reacted with phenylboronic acid (1 to 1.5 equivalents) and a catalytic amount of tetrakis(triphenylphosphine) palladium [Pd(PPh$_3$)$_4$, 0.01 to 0.05 equivalents]. The reaction is conveniently performed in a biphasic solvent mixture consisting of benzene or toluene and aqueous sodium carbonate at a temperature range of 50° to 130° C.

Further, when an optically-active form of a compound of formula (I) is required, a racemic form of said compound may be reacted with an optically active form of a suitable organic base, for example, brucine, coniine, 2-pipecoline or N,N,N-trimethyl-(1-phenylethyl)ammonium hydroxide followed by conventional separation of the diasteriomeric mixture of salts or complexes thus obtained, for example, by fractional crystallization from a suitable solvent, for example, a lower alkanol, whereafter the optically active form of said compound may be liberated by treatment with acid using a conventional procedure, for example, using an aqueous mineral acid such as dilute hydrochloric acid.

The following Examples further illustrate this invention.

EXAMPLE 1

4-Chloro-2-cyanobenzoic Acid, Methyl Ester

[(XI), R'=CH$_3$, X=4—Cl, Y=H]

Water (540 mL) was added to a suspension of 2-amino-4-chlorobenzoic acid, methyl ester [(XV), R$^1$=CH$_3$, X=4—Cl, Y=H, 20.0 g, 0.108 mol] in concentrated aqueous HCl (65 mL) and this suspension was cooled, with stirring, below 5° C. A solution of sodium nitrite (7.4 g, 0.108 mol) in water (20 mL) was added dropwise over a 10 minute period at 0°–5° C. until complete dissolution had occurred. This diazonium solution was then brought to pH 6 with saturated aqueous sodium carbonate.

In a separate reaction vessel a solution of copper sulfate pentahydrate (32.3 g, 0.129 mol) in water (130 mL) was added dropwise to a stirred, 0°–5° C. solution of potassium cyanide (32.3 g, 0.496 mol) in 65 mL of water. Benzene was added to the resulting brown suspension and this biphasic mixture was then heated in a 60° C. oil bath.

The previously prepared diazonium solution was then added dropwise to this brown, copper (I) cyanide containing solution at 60° C. over a 40 minute period. The reaction mixture was then heated at 70° C. for an additional hour. The reaction mixture was then cooled to room temperature and ethyl acetate (1 L) was added. This biphasic mixture was filtered through celite. The layers were separated and the ethyl acetate layer was washed with brine and dried (MgSO$_4$). The solvent was removed and the solid was triturated with petroleum ether to provide the product (15.8 g, 75%) as a tan solid.

A small portion was recrystallized from petroleum ether: chloroform to afford colorless plates, m.p. 115°–117° C.

EXAMPLES 2 TO 8

By a procedure similar to that described in Example 1, the following compounds of formula (XI) were prepared starting from the appropriate substituted 2-aminobenzoic acid, ester of formula (XV).

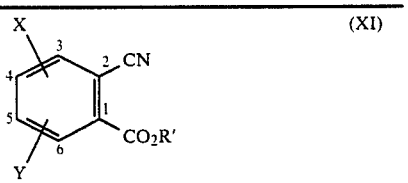

| Example | R' | X | Y | m.p. °C. (recrystallization solvent) |
|---|---|---|---|---|
| 2 | $CH_2CH_3$ | 5-Cl | H | 95–98(petroleum ether:benzene) |
| 3 | $CH_2CH_3$ | 4,5-CH=CH—CH=CH | | 89–90 |
| 4 | $CH_2CH_3$ | 3-Cl | H | 104–108 |
| 5 | $CH_3$ | 6-Cl | H | (note 1) |
| 6 | $CH_2CH_3$ | 5-Br | H | 93–96 |
| 7 | $CH_3$ | 5-$CH_3$ | H | (note 2) |
| 8 | $CH_3$ | 4-$CO_2CH_3$ | H | 117 |

Notes
1. NMR ($d^6$DMSO, 200MHz): δ 3.97 (s, 3H, C$\underline{H}_3$), 7.75 (t, 1H), 7.98 (d, 1H), 8.02(d, 1H)
2. NMR ($d^6$DMSO, 200MHz): δ 2.45(s, 3H, C$\underline{H}_3$), 3.91 (s, 3H, OC$\underline{H}_3$), 7.69 (d, 1H), 7.94(d, 1H), 7.98 (s, 1H)

EXAMPLE 9

2-Cyano-5-methoxybenzoic Acid, Methyl Ester

[(XI), R'=$CH_3$, X=5—$OCH_3$, Y=H]

Copper (I) cyanide (6.03 g, 67.3 mmol) was added to a stirred solution of 2-bromo-5-methoxybenzoic acid, methyl ester [(XVI), R'=$CH_3$, X=5—$OCH_3$, Y=H, Z=Br, 15.0 g, 61.2 mmol] and 1-methyl-2-pyrolidinone (35 mL) under a dry $N_2$ atmosphere. The suspension was heated to reflux temperature for 25 minutes and then cooled to room temperature. The reaction mixture was diluted with water (700 mL) and filtered. The solid cake was added to a stirred solution of sodium cyanide (35 g) in water (1.1 L). This suspension was stirred rapidly at room temperature for 40 minutes. This suspension was then diluted with ethyl acetate (300 mL) and filtered through celite. The layers were separated and the aqueous layer was extracted with ethyl acetate (300 mL). The combined ethyl acetate phase was washed with brine and dried ($MgSO_4$). The solvent was removed to provide the product (7.7 g, 66%) as an off white solid, m.p. 74°–77° C.

EXAMPLES 10 TO 13

By a procedure similar to that described in Example 9, the following compounds of formula (XI) were prepared starting from the appropriate substituted 2-halobenzoic acid ester of formula (XVI).

| Example | Type of halogen Z in starting material | R' | X | Y | m.p. °C. |
|---|---|---|---|---|---|
| 10 | Cl | $CH_3$ | 4-F | H | 104–106 |
| 11 | Cl | $CH_3$ | 5-$SCH_3$ | H | 75–77 |
| 12 | Cl | $CH_3$ | 4-$NO_2$ | H | 111–115 |
| 13 | Cl | $CH_3$ | 6-$CH_3$ | H | (note 1) |

Notes
1. NMR ($CDCl_3$, 200MHz): δ 2.46 (s, 3H, C$\underline{H}_3$), 3.99 (s, 3H, $CO_2C\underline{H}_3$), 7.4–7.6 (m, 3H)

EXAMPLE 14

2-Cyano-4,5-dichlorobenzoic Acid, Methyl Ester

[(XI), R'=$CH_3$, X=4—Cl, Y=5—Cl]

(a) Preparation of 4,5-Dichlorophthalic Acid, Anhydride [(XVIII), X=4—Cl, Y=5—Cl]

A suspension of 4,5-dichlorophthalic acid [(XVII), X=4—Cl, Y=5—Cl, 50.0 g, 0.213 mol] and acetic anhydride (70 mL) was heated to reflux until dissolution occurred. A distilling head was then attached and 30 mL of distillate was removed. The solution was cooled to room temperature whereupon a precipitate appeared. This solid was filtered, washed with anhydrous ether and dried in vacuo to provide the product (40.4 g, 87%) as a tan solid, m.p. 189°–192° C.

(b) Preparation of 2-Carbamoyl-4,5-dichlorobenzoic Acid [(XIX), X=4—Cl, Y=5—Cl]

4,5-Dichlorophthalic acid, anhydride (20.0 g, 92.2 mmol) was dissolved in dry THF (400 mL) and cooled in an ice bath. Ammonia gas was then passed through this solution for 10 minutes to afford a precipitate. The THF was removed and water (400 mL) was added. This aqueous solution was brought to acidic pH with 10% aqueous HCl whereupon a precipitate appeared. This solid was collected, washed with water and dried in vacuo to provide the product (17.3 g, 80%) as a tan solid, m.p. 197°–201° C.

(c) Preparation of 2-Cyano-4,5-dichlorobenzoic Acid, Methyl Ester

Triethylamine (25.4 mL, 0.182 mol) was added dropwise over a 20 minute period to a cold (0°–5° C.), stirred suspension of 2-carbamoyl-4,5-dichlorobenzoic acid (21.3 g, 91.0 mmol) in dichloromethane (110 mL). Methyl chloroformate (15.5 mL, 0.2 mol) was then added dropwise over a 30 minute period. The reaction mixture was then warmed to room temperature and stirred overnight. The solvents were removed and water (200 mL) was added. The water phase was filtered and the precipitate was washed with water and dried in vacuo to provide the product (20.5 g, 97%) as a tan solid, m.p. 120°–123° C.

EXAMPLE 15

2-Cyano-5-phenylbenzoic Acid, Ethyl Ester

[(XI), X=5—Ph, Y=H, R'=Et]

A solution of phenylboronic acid (4.69 g, 38.5 mmol) in ethanol (20 mL) was added to a rapidly stirred suspension of 5-bromo-2-cyanobenzoic acid, ethyl ester

[(XI), X=5—Br, Y=H, R'=Et (prepared according to Example 6), 8.9 g, 35.0 mmol], tetrakis(triphenylphosphine)palladium (1.21 g, 1.05 mmol), benzene (70 mL) and 2.0M aqueous Na₂CO₃ (35 mL). This biphasic mixture was heated to reflux and stirred for 4 hours under a dry N₂ atmosphere.

The reaction mixture was cooled to room temperature, 30% hydrogen peroxide (16 mL) was added and the suspension was stirred at room temperature for 1 hour. The product was extracted with ether (3×100 mL) and the combined ether phase was washed with brine (200 mL) and dried (MgSO₄). Silica gel (150 mL) was added and the solvent was removed. The silica absorbate was flash chromatographed (silica, 9:1 petroleum ether: ethyl acetate as eluent) to provide the product as a white solid (6.37 g, 72%), m.p. 69°–74° C.

EXAMPLE 16

5-Chloro-3-imino-1-oxoisoindoline

[(XII), X=5—Cl, Y=H]

A solution of 4-chloro-2-cyanobenzoic acid, methyl ester [(XI), R'=CH₃, X=5—Cl, Y=H, prepared according to Example 1, 16.9 g, 86.5 mmol] in methanol (800 mL) was cooled in an ice bath. Ammonia gas was passed through this solution over a 30 minute period. The solution was then allowed to sit at room temperature for 3 days. The resulting precipitate was then collected, washed with ether and dried in vacuo to provide the product (12.5 g, 80%) as a tan solid, m.p. 295°–296° C. (dec.).

EXAMPLES 17 TO 30

By a procedure similar to that described in Example 16, the following compounds of formula (XII) were prepared starting from the appropriate substituted 2-cyanobenzoic acid ester of formula (XI).

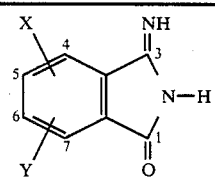

| Example | Example of Starting Material | X | Y | m.p. °C. |
|---|---|---|---|---|
| 17 | 2 | 6-Cl | H | 255-264 |
| 18 | 14 | 5-Cl | 6-Cl | 330-335(dec.) |
| 19 | 10 | 5-F | H | 270-272 |
| 20 | 3 | 5,6-CH=CH—CH=CH | | 275-278(dec.) |
| 21 | 4 | 4-Cl | H | 236-240 |
| 22 | 5 | 7-Cl | H | 272-273 |
| 23 | 6 | 6-Br | H | 245-255 |
| 24 | 9 | 6-OCH₃ | H | 247-250 |
| 25 | 11 | 6-SCH₃ | H | 255-260 |
| 26 | 12 | 5-NO₂ | H | 295-305(dec.) |
| 27 | 7 | 6-CH₃ | H | 237-240 |
| 28 | 8 | 5-CO₂CH₃ | H | 276-281 |
| 29 | 13 | 7-CH₃ | H | 241-244(dec.) |
| 30 | 15 | 6-Ph | H | 269-272 |

EXAMPLE 31

Cyano-(6-chloro-2,3-dihydro-3-oxo-isoindole-1-ylidene)-acetic Acid, Ethyl Ester

[(XIV), R'=CH₂CH₃, X=6—Cl, Y=H]

A suspension of 5-chloro-3-imino-1-oxoisoindoline [(XII), X=5—Cl, Y=H, prepared according to Example 16, 5.0 g, 27.6 mmol] in ethyl cyanoacetate (11.7 mL, 0.110 mol) was placed in a 180° C. oil bath under a dry N₂ atmosphere and heated for 10 minutes. After that period the internal temperature reached 160° C. The reaction mixture was cooled to room temperature and the solid was collected, broken up and triturated with ether to provide the product (7.1 g, 93%) as an off-white solid, m.p. 179°–181° C.

EXAMPLES 32 TO 45

By a procedure similar to that described in Example 31, the following compounds of formula (XIV) were prepared from the approriate substituted 3-imino-1H-isoindole-1-one of formula (XII).

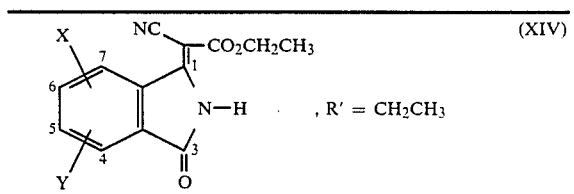

| Example | Example of Starting Material | X | Y | m.p. °C. |
|---|---|---|---|---|
| 32 | 17 | 5-Cl | H | 208-211 (methanol) |
| 33 | 18 | 5-Cl | 6-Cl | 236-243 (hexane:CHCl₃) |
| 34 | 19 | 6-F | H | 175-178 |
| 35 | 20 | 5,6-CH=CH—CH=CH | | 233-240 |
| 36 | 21 | 7-Cl | H | 133-135 |
| 37 | 22 | 4-Cl | H | 186-187 |
| 38 | 23 | 5-Br | H | 227-230 |
| 39 | 24 | 5-OCH₃ | H | 192-198 |
| 40 | 25 | 5-SCH₃ | H | 255-260 |
| 41 | 26 | 6-NO₂ | H | 170-172 |
| 42 | 27 | 5-CH₃ | H | 237-240 |
| 43 | 28 | 6-CO₂CH₃ | H | 197-200 |
| 44 | 29 | 4-CH₃ | H | 197-202 |
| 45 | 30 | 5-Ph | H | 204-205 |

EXAMPLE 46

Cyano-(6-chloro-2,3-dihydro-3-oxo-isoindole-1-ylidene)-acetic Acid, Ethyl Ester

[(IV), A=CO, R=CH₃, R'=CH₂CH₃, X=6—Cl, Y=H]

A suspension of cyano-(6-chloro-2,3-dihydro-3-oxo-isoindole-1-ylidene)-acetic acid, ethyl ester [(XIV), R'=CH₂CH₃, X=6—Cl, Y=H, prepared according to Example 31, 7.8 g, 28.0 mmol], iodomethane (2.3 mL, 36.4 mmol) and potassium carbonate (3.87 g, 28.0 mmol) in dry DMF (39 mL) was heated, with stirring, under a dry N₂ atmosphere, in a 100° C. oil bath for 1 hour. The reaction mixture was cooled to room temperature and added to water (500 mL). The water phase was extracted with ether (3×200 mL). The combined ether phase was washed with brine, dried (MgSO₄) and the solvent was removed to provide the product (7.4 g, 91%) as a light yellow solid and as a mixture of double bond regioisomers.

NMR (d⁶DMSO, 200 MHz): δ1.31, 1.32 (2t, 3H, CH₂C$\underline{H}$₃), 3.17, 3.52 (2s, 3H, N—CH₃), 4.33, 4.37 (2q, 2H, C$\underline{H}$₂CH₃), 7.8–8.0 (m, 2H), 8.33, 8.40 (2s, 1H)

EXAMPLES 47 TO 66

By a procedure similar to that described in Example 46, the following compounds of formula (IV) (A=CO) were prepared from the appropriate substituted cyano-(6-chloro-2,3-dihydro-3-oxo-isoindole-1-ylidene)acetic acid, ethyl ester of formula (XIV) and the appropriate alkylating agent. The compounds of formula (IV) (A=CO) were generally obtained as a mixture of geometrical isomers and were used without purification in the next step.

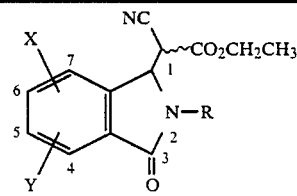

(IV), A = CO, R' = CH₂CH₃

| Example | Alkylating Agent | Example of Starting Material | R | X | Y | NMR (note 2) |
|---|---|---|---|---|---|---|
| 47 | benzyl-bromide | (note 1) | CH₂Ph | H | H | 1.05, 1.27(2t, 3H, CH₂C$\underline{H}$₃), 4.04, 4.35(2q, 2H, C$\underline{H}$₂CH₃), 5.21, 5.40(2s, 2H, NC$\underline{H}$₂), 6.9–7.5(m, 5H), 7.8–8.6(m, 4H) |
| 48 | α,3,4-tri-chlorotoluene | (note 1) | | H | H | 1.08, 1.30(2t, 3H, CH₂C$\underline{H}$₃), 4.05, 4.38(2q, 2H, C$\underline{H}$₂CH₃), 5.12, 5.35(2s, 2H, NC$\underline{H}$₂), 7.0–8.1(m, 6H), 8.55(d, 1H) |
| 49 | 4-bromo-2-fluoro-benzylbromide | (note 1) | | H | H | 1.12, 1.30(2t, 3H, CH₂C$\underline{H}$₃), 4.10, 4.35(2q, 2H, C$\underline{H}$₂CH₃), 5.17, 5.33(2s, 3H, NC$\underline{H}$₂), 7.08(t, 1H), 7.35(d, 1H), 7.56(d, 1H), 7.8–8.1(m, 3H), 8.55(d, 1H) |
| 50 | iodomethane | (note 1) | CH₃ | H | H | 1.31(t, 3H, CH₂C$\underline{H}$₃), 3.17, 3.52(2s, 3H, NC$\underline{H}$₃), 4.2–4.5(m, 2H, C$\underline{H}$₂CH₃), 7.7–8.5(m, 4H) |
| 51 | 2-chloro-6-fluoro-benzylbromide | (note 1) | 2-Cl, 6-F benzyl (CH₂-C₆H₃ClF) | H | H | 1.15, 1.30(2t, 3H, CH₂C$\underline{H}$₃), 4.15, 4.32(2q, 2H, C$\underline{H}$₂CH₃), 5.27, 5.47(2s, 3H, NC$\underline{H}$₂), 7.1–7.5(m, 3H), 7.8–8.1(m, 3H), 8.4–8.6 (m, 1H) |
| 52 | iodobutane | (note 1) | (CH₂)₃CH₃ | H | H | 0.80–1.80 (m, 10H, OCH₂CH₃, NCH₂—(C$\underline{H}$₂)₂C$\underline{H}$₃), 3.89, 4.07(2t, 2H, NC$\underline{H}$₂), 4.2–4.5(m, 2H, OC$\underline{H}$₂CH₃), 7.7–8.6(m, 4H) |
| 53 | iodomethane | 32 | CH₃ | 5-Cl | H | 1.31, 1.32(2t, 3H, CH₂C$\underline{H}$₃), 3.18, 3.53(2s, 3H, NC$\underline{H}$₃), 4.34, 4.38(2q, 2H, C$\underline{H}$₂CH₃), 7.8–8.1(m, 2H), 8.22, 8.43(2d, 1H) |
| 54 | 4-bromo-2-fluoro-benzylbromide | 31 | 4-Br, 2-F benzyl (CH₂-C₆H₃BrF) | 6-Cl | H | 1.10, 1.27(2t, 3H, CH₂C$\underline{H}$₃), 4.08, 4.36(2q, 2H, C$\underline{H}$₂CH₃), 5.15, 5.34(2s, 2H, NC$\underline{H}$₂), 7.10(m, 1H), 7.3–7.7(m, 2H), 7.9–8.5(m, 3H) |
| 55 | iodomethane | 33 | CH₃ | 5-Cl | 6-Cl | 1.29, 1.30(2t, 3H, CH₂C$\underline{H}$₃), 3.18, 3.50(2s, 3H, NC$\underline{H}$₃), 4.33, 4.37(2q, 2H, C$\underline{H}$₂CH₃), 8.18, 8.24(2s, 1H), 8.53(s, 1H) |
| 56 | iodomethane | 34 | CH₃ | 6-F | H | 1.33, 1.34(2T, 3H, CH₂C$\underline{H}$₃), 3.20, 3.55(2s, 3H, NC$\underline{H}$₃), 4.36, 4.40(2q, 2H, C$\underline{H}$₂CH₃), 7.6–7.8(m, 1H), 7.9–8.2(m, 2H) |
| 57 | iodomethane | 35 | CH₃ | 5,6-CH=CH—CH=CH | | (CDCL₃)1.41, 1.45(2t, 3H, CH₂C$\underline{H}$₃), 3.37, 3.75(2s, 3H, NC$\underline{H}$₃), 4.38, 4.45(2q, 2H, C$\underline{H}$₂CH₃), 7.6–7.8(m, 2H), 7.9–8.2(m, 2H), |

-continued

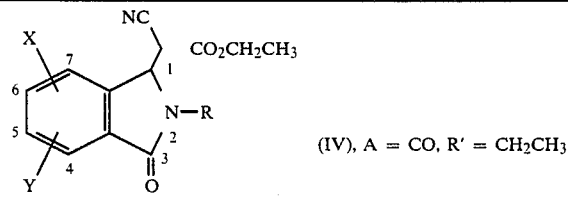

(IV), A = CO, R' = CH$_2$CH$_3$

| Example | Alkylating Agent | Example of Starting Material | R | X | Y | NMR (note 2) |
|---|---|---|---|---|---|---|
| | | | | | | 8.37, 8.39(2s, 1H), 9.07, 9.13(2s, 1H) |
| 58 | iodomethane | 36 | CH$_3$ | 7-Cl | H | 0.95(t, 3H, CH$_2$C$\underline{H}_3$), 2.76, 3.24(2s, 3H, NC$\underline{H}_3$), 4.01(q, 2H, C$\underline{H}_2$CH$_3$), 7.5–7.9(m, 3H) |
| 59 | iodomethane | 37 | CH$_3$ | 4-Cl | H | 1.31(t, 3H, CH$_2$C$\underline{H}_3$), 3.16, 3.51(2s, 3H, NC$\underline{H}_3$), 4.34, 4.38(2q, 2H, C$\underline{H}_2$CH$_3$), 7.7–8.0(m, 2H), 8.14, 8.47(2dd, 1H) |
| 60 | iodomethane | 38 | CH$_3$ | 5-Br | H | 1.30(t, 3H, CH$_2$C$\underline{H}_3$), 3.17, 3.52(2s, 3H, NC$\underline{H}_3$), 4.32(q, 2H, C$\underline{H}_2$CH$_3$), 7.9–8.2(m, 2H), 8.33, 8.38(2s, 1H) |
| 61 | iodoethane | 31 | CH$_2$CH$_3$ | 6-Cl | H | 1.0–1.4(m, 4H, OCH$_2$C$\underline{H}_3$, NCH$_2$C$\underline{H}_2$), 3.90, 4.17(2q, 2H, NC$\underline{H}_2$CH$_3$), 4.37, 4.40(2q, 2H, OC$\underline{H}_2$CH$_3$), 7.8–8.0(m, 2H), 8.29, 8.50(2d, 1H) |
| 62 | iodomethane | 39 | CH$_3$ | 5-OCH$_3$ | H | 1.30(t, 3H, CH$_2$C$\underline{H}_3$), 3.16, 3.50(2s, 3H, NC$\underline{H}_3$), 3.91, 3.92(2s, 3H, OC$\underline{H}_3$), 4.31, 4.34(2q, 2H, C$\underline{H}_2$CH$_3$), 7.2–7.6(m, 2H), 8.17, 8.36(2d, 1H) |
| 63 | iodomethane | 40 | CH$_3$ | 5-SCH$_3$ | H | 1.30(t, 3H, CH$_2$C$\underline{H}_3$), 2.60(s, 3H, SC$\underline{H}_3$), 3.15, 3.50(2s, 3H, N—C$\underline{H}_3$), 4.31, 4.35(2q, 2H, C$\underline{H}_2$CH$_3$), 7.5–7.8(m, 2H), 8.09, 8.31(2d, 1H) |
| 64 | iodopropane | 33 | CH$_2$CH$_2$CH$_3$ | 5-Cl | 6-Cl | 0.79, 0.89(2t, 3H, N(CH$_2$)$_2$C$\underline{H}_3$), 1.32(t, 3H, OCH$_2$C$\underline{H}_3$), 1.48, 1.70(2sex, 2H, N—CH$_2$C$\underline{H}_2$CH$_3$), 3.84, 4.04(2t, 2H, N—C$\underline{H}_2$—CH$_2$), 4.38(q, 3H,OC$\underline{H}_2$CH$_3$), 8.18, 8.28(2s, 1H), 8.47, 8.62(2s, 1H) |
| 65 | iodomethane | 41 | CH$_3$ | 6-NO$_2$ | H | 1.32, 1.35(2t, 3H, CH$_2$C$\underline{H}_3$), 3.23, 3.58(2s, 3H, NC$\underline{H}_3$), 3.37, 3.42(2q, 2H, C$\underline{H}_2$CH$_3$), 8.1–8.3(m, 1H), 8.5–8.7(m, 1H), 9.15, 9.22(2d, 1H) |
| 66 | iodomethane | 42 | CH$_3$ | 5-CH$_3$ | H | 1.30(t, 3H, CH$_2$C$\underline{H}_3$), 2.45, 2.48(2s, 3H, C$\underline{H}_3$), 3.16, 3.50(2s, 3H, NC$\underline{H}_3$), 4.31, 4.36(2q, 2H, C$\underline{H}_2$CH$_3$), 7.5–7.75(m, 1H), 7.75, 7.94(2s, 1H), 8.10, 8.32(2d, 1H) |
| 67 | iodomethane | 43 | CH$_3$ | 6-CO$_2$CH$_3$ | H | 1.32, 1.34(2t, 3H, CH$_2$C$\underline{H}_3$), 3.20, 3.55(2s, 3H, NC$\underline{H}_3$), 3.92, 3.93(2s, 3H, CO$_2$C$\underline{H}_3$), 4.35, 4.40(2q, 2H, C$\underline{H}_2$CH$_3$), 8.0–8.4 (m, 2H), 8.79, 9.06(2s, 1H) |
| 68 | iodomethane | 44 | CH$_3$ | 4-CH$_3$ | H | 1.30(t, 3H, CH$_2$C$\underline{H}_3$), 2.61, 2.62(2s, 3H, C$\underline{H}_3$), 3.15, 3.50(2s, 3H, NC$\underline{H}_3$), 4.31, 4.37(2q, 2H, C$\underline{H}_2$CH$_3$), 7.5–7.8(m, 2H), 8.00, 8.33(2d, 1H) |
| 69 | iodomethane | 45 | CH$_3$ | 5-Ph | H | 1.32, 1.33(2t, 3H, CH$_2$C$\underline{H}_3$), 3.20, 3.55(2s, 3H, NC$\underline{H}_3$), 4.33, 4.39(2q, 2H, C$\underline{H}_2$CH$_3$), 7.4–8.6(m, |

-continued

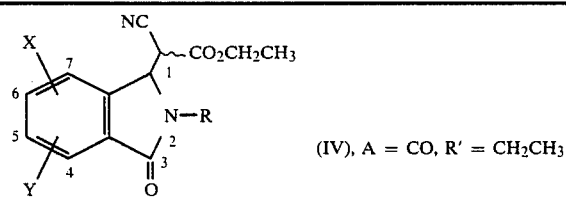

(IV), A = CO, R' = CH₂CH₃

| Example | Alkylating Agent | Example of Starting Material | R | X | Y | NMR (note 2) |
|---------|------------------|------------------------------|---|---|---|--------------|
|         |                  |                              |   |   |   | 8H)          |

Notes
(1) Prepared according to procedure of J. Kranz, Chem. Ber., 106, 2261(1967).
(2) NMR spectra were recorded on a 200 MHz instrument in d⁶DMSO solvent unless otherwise indicated.

EXAMPLE 70

2-[(4-Bromo-2-fluorophenyl)methyl]-benzothiazolin-3-one, 1,1-Dioxide

[(VIII), R=

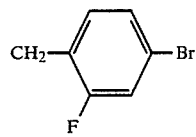

, X=Y=H]

A stirred suspension of sodium saccharin (VII, M=Na, 10.0 g, 48.7 mmol) and 4-bromo-2-fluorobenzylbromide (12.96 g, 48.7 mmol) in dry DMF was heated in a 100° C. oil bath under a dry N₂ atmosphere. Dissolution occurred within 10 minutes and after 1 hour the reaction mixture was cooled to room temperature and added to water (600 mL). The resulting solid was filtered, washed well with water and dried in vacuo to provide the product (17.1 g, 95%) as a white solid, m.p. 177°–182° C.

EXAMPLES 71 TO 78

By a procedure similar to that described in Example 70, the compounds of formula (VIII) were prepared from sodium saccharin and the appropriate alkylating agent.

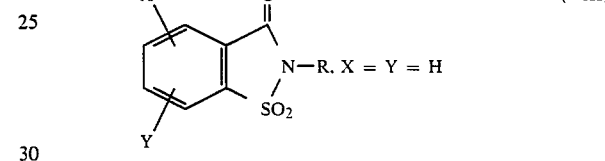

| Example | Alkylating Agent | R | m.p. °C. |
|---------|------------------|---|----------|
| 71 | α,3,4,-trichlorotoluene | CH₂-C₆H₃(Cl)(Cl) | 142–146 |
| 72 | 4-bromobenzylbromide | CH₂-C₆H₄-Br | 158–165 |
| 73 | iodobutane | CH₂(CH₂)₂CH₃ | 41–44 |
| 74 | 2-fluorobenzylbromide | CH₂-C₆H₄-F | 95–102 |
| 75 | 2-chloro-6-fluorobenzylbromide | CH₂-C₆H₃(Cl)(F) | 187–190 |
| 76 | 2-iodopropane | CH(CH₃)₂ | 55–62 |
| 77 | 1-bromo-2-bromomethylnaphthalene | CH₂-(2-Br-naphthyl) | 206–210 |
| 78 | 2-bromoethylnaphthalene | CH₂-naphthyl | 136–146 |

EXAMPLE 79

2[[[(4-Bromo-2-fluorophenyl)methyl]amino]sulfonyl]-α-cyano-β-oxobenzenepropanoic Acid, Ethyl Ester [(IX), R=

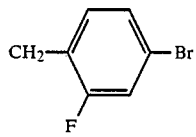

, R'=CH₂CH₃, X=Y=H]

Ethyl cyanoacetate (14.9 mL, 0.140 mol) was added dropwise, over a 20 minute period, to a stirred, room temperature suspension of potassium t-butoxide (15.1 g, 0.134 mol) in dry THF (85 mL) under a dry N₂ atmosphere. This suspension was then heated in a 60° C. oil bath for 45 minutes and then cooled to room temperature. To this suspension was added a solution of 2-[(4-bromo-2-fluorophenyl)methyl]benzothiazolin-3-one 1,1-dioxide [(VIII), prepared according to Example 70, 16.5 g, 44.7 mmol] in dry THF (190 mL), dropwise over a 10 minute period. The resulting suspension was heated to reflux temperature for 3 hours and then cooled to room temperature. The reaction mixture was diluted with water (2 L), acidified to pH 1 with concentrated aqueous HCl and then heated on a hot plate with rapid stirring for 10 minutes. The cooled suspension was filtered and the solid was washed with water and dried in vacuo to provide the product (19.8 g, 91%) as a white solid, m.p. 123°–124° C.

EXAMPLES 80 TO 89

By procedure similar to that described in Example 79, the compounds of formula (IX) were prepared from the appropriate substituted benzothiazoline-3-one 1,1-dioxide of formula (VIII).

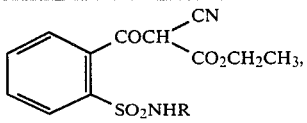

R' = CH₂CH₃, X = Y = H

| Example | Example of Starting Material | R | m.p. °C. |
|---|---|---|---|
| 80 | (Note 1) | CH₂Ph | 146–148 |
| 81 | 71 | 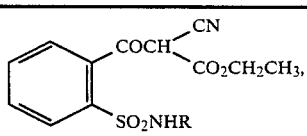 | 144–145 |
| 82 | 72 | CH₂—⌬—Br | 138–145 |
| 83 | (Note 2) | CH₂CH₃ | 160–166 |
| 84 | 73 | CH₂(CH₂)₂CH₃ | 124–127 |
| 85 | 74 | CH₂—⌬(F) | 136–140 |
| 86 | 75 | CH₂—⌬(F,Cl) | 137–143 |
| 87 | 76 | CH(CH₃)₂ | 116–119 |
| 88 | 77 | CH₂—naphthyl-Br | 163–166 |
| 89 | 78 | CH₂—naphthyl | 141–145 |

Notes
(1) H. Eckenroth, G. Koerppen, Ber., 29, 1048(1986).
(2) F. Sachs, F. von Wolff, A. Ludwig, Ber., 37, 3252(1904).

EXAMPLE 90

[2-[(4-Bromo-2-fluorophenyl)methyl]-3-benzothiazolylidine]-α-cyanoacetic Acid, Ethyl Ester 1,1-Dioxide

[(IV), A=SO₂, R=

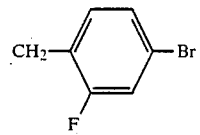

, R'=CH₂CH₃, X=Y=H]

A solution of 2-[[[(4-bromo-2-fluorophenyl)methyl]amino]sulfonyl-α-cyano-β-oxobenzenepropanoic acid, ethyl ester [(IX), prepared according to Example 79, 17.6 g, 36.4 mol] in acetic anhydride was heated to reflux for 50 minutes and then cooled to room temperature. The reaction mixture was added to water and stirred for 15 minutes. The suspension was filtered and the solid was washed with water and dried in vacuo. The solid product was flash chromatographed (4:1 petroleum ether: ethyl acetate on silica gel) to provide the product (12.4 g, 73%) as a white solid. A small portion (3.1 g) was again flash chromatographed (1:1 petroleum ether: dichloromethane) to provide the product (1.9 g) as a white solid, m.p. 161°–164° C.

EXAMPLES 91 TO 100

By a procedure similar to that described in Example 90, the compounds of formula (IV) (A is $SO_2$) were prepared from the appropriate substituted 2-aminosulfonyl-α-cyano-β-oxobenzenepropanoic acid, ethyl ester of formula (IX). The compounds of formula (IV) (A is $SO_2$) were generally obtained as mixtures of geometric isomers contaminated with varying amounts of the appropriately substituted compound of formula (VIII) and were used without purification in the next step.

$$\text{(IV)}$$

A = $SO_2$, R' = $CH_2CH_3$, X = Y = H

| Example | Example of Starting Material | R | m.p. °C. |
|---|---|---|---|
| 91 | 80 | $CH_2Ph$ | 171–174 |
| 92 | 81 | $CH_2$-(2,3-dichlorophenyl) | 183–184 |
| 93 | 82 | $CH_2$-(4-bromophenyl) | — |
| 94 | 83 | $CH_2CH_3$ | — |
| 95 | 84 | $CH_2(CH_2)_2CH_3$ | — |
| 96 | 85 | $CH_2$-(2-fluorophenyl) | — |
| 97 | 86 | $CH_2$-(2-chloro-4-fluorophenyl) | — |
| 98 | 87 | $CH_2(CH_3)_2$ | — |
| 99 | 88 | $CH_2$-(1-bromonaphth-2-yl) | 172–175 |
| 100 | 80 | $CH_2$-(naphth-2-yl) | — |

EXAMPLE 101

2,3-Dihydro-2-methylspiro[benzisothiazole-3,3'-pyrrolidine]-2',5'-dione 1,1-Dioxide

[(I), A=$SO_2$, R=$CH_3$, X=Y=H]

Potassium cyanide (1.30 g, 20.0 mmol) was added to a suspension of 2-methyl-3-benzothiazolylidine]-α-cyanoacetic acid, ethyl ester 1,1-dioxide [(IV), A=$SO_2$, R=$CH_3$, R'=$CH_2CH_3$, X=Y=H, prepared according to the procedure of C. Melchiorre et al, Ann. Chim. (Rome) 61 (6), 1971, 5.56 g, 19.0 mmol] in methanol (160 mL) under an $N_2$ atmosphere. The mixture was stirred at room temperature for 3 hours and then cooled in an ice bath. Hydrogen chloride gas was then passed through the reaction mixture for 0.5 hours. After stading at room temperature for 3 days, the reaction mixture was heated to reflux for 1 hour. After cooling to room temperature, the methanol was removed and the residue was diluted with water (160 mL). The organics were extracted with ethyl acetate and the combined extracts were dried ($MgSO_4$) and the solvent was removed. The residual solid was dissolved in glacial acetic acid (150 mL) and heated to reflux for 4 hours under a $N_2$ atmosphere. The acetic acid was removed and the residual solid was triturated with petroleum ether, chloroform, ether, and boiling ethanol to give the product (2.89 g, 57%) as a white solid, m.p. 288°–293° C.

Anal. Calcd. for $C_{11}H_{10}N_2O_4S \cdot \frac{1}{4}H_2O$: C, 48.79; H, 3.92; N, 10.35%. Found: C, 48.96; H, 3.90; N, 10.58%.

EXAMPLE 102

6-Chloro-2-methylspiro[1H-isoindole-1,3'-pyrrolidine]-2',3,5'(2H)-trione

[(I), A=CO, R=$CH_3$, X=6—Cl, Y=H]

Potassium cyanide (1.75 g, 26.7 mol) was added to a stirred, room temperature suspension of 6-chloro-α-cyano-2-methyl-3-oxo-$\Delta^1$-α-isoindolineacetic acid, ethyl ester [(IV), A=CO, R=$CH_3$, R'=$CH_2CH_3$, X=6—Cl, Y=H, prepared according to the procedure of Example 46, 7.40 g, 25.5 mmol] in dry DMSO (180 mL). After 2 hours the reaction mixture was added to water (1 L) and extracted with ether (3×25 mL). These ether extracts were discarded. The aqueous solution was cautiously acidified with 10% aqueous HCl to pH 1. The resulting precipitate was collected, washed with water and dried in vacuo to give 6-chloro-1-cyano-2-methyl-3-oxo-1-isoindolinylcyanoacetic acid, ethyl ester [formula (V), A=CO, R=$CH_3$, R'=$CH_2CH_3$, X=6—Cl, Y=H, 7.1 g, 88%] which was used without purification in the next step.

A suspension of the above compound [formula (V), A=CO, R=$CH_3$, R'=$CH_2CH_3$, X=6—Cl, Y=H, 7.1 g, 22.5 mmol] in dry methanol (225 mL) was cooled in an ice bath. Hydrogen chloride gas was passed through this suspension and within 5 minutes dissolution occurred. After an additional 15 minutes of purging the solution with HCl gas, the reaction mixture was allowed to sit at room temperature for 3 days. This solution was then heated to reflux for 4 hours and then cooled to room temperature. The methanol was removed, water (200 mL) was added and the organics were extracted with ethyl acetate (3×100 mL). The combined ethyl acetate extracts were dried ($MgSO_4$) and concentrated to provide a yellow solid (7.7 g), containing 6-chloro-4'-methoxycarbonyl-2-methyl-spiro[1H-isoindole-1,3'-pyrrolidine]-2',3,5'(2H)-trione

[formula (VI), A=CO, R=CH₃, R″=CH₃, X=6—Cl, Y=H].

The above solid containing the compound of formula (VI) (A=CO, R=CH₃, R″=CH₃, X=6—Cl, Y=H) was dissolved in glacial acetic acid and heated to reflux for 4.5 hours. After cooling to room temperature and standing overnight, the reaction mixture was filtered and the solid product was washed well with ether to provide the title compound (4.45 g, 60%) as a white solid, m.p. 339°–343° C. (dec.).

Anal. Calcd. for $C_{12}H_9ClN_2O_3$: C, 54.46; H, 3.43; N, 10.58%. Found: C, 54.25; H, 3.58; N, 10.53%.

EXAMPLES 103 TO 136

By a procedure similar to that described in Example 102, the compounds of formula (I) were prepared from the appropriate compounds of formula (IV).

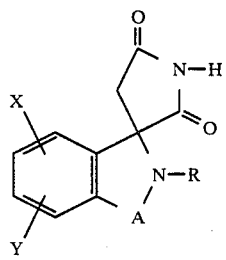

(I)

| Example | Example of Starting Material | A | R | X | Y | m.p. °C. | Analysis % Calcd.(upper) Found(lower) C | H | N |
|---|---|---|---|---|---|---|---|---|---|
| 103 | 91 | SO₂ | CH₂Ph | H | H | 205–208 | 59.64 | 4.12 | 8.18 |
|  |  |  |  |  |  |  | 59.58 | 4.36 | 8.01 |
| 104 | 90 | SO₂ | CH₂-C₆H₃(F)-Br | H | H | 120–123 | 46.48 | 2.75 | 6.38 |
|  |  |  |  |  |  |  | 46.23 | 2.83 | 6.35 |
| 105 | 92 | SO₂ | CH₂-C₆H₃(Cl)-Cl | H | H | 197–198 | 49.65 | 2.94 | 6.81 |
|  |  |  |  |  |  |  | 49.41 | 3.03 | 6.55 |
| 106 | 93 | SO₂ | CH₂-C₆H₄-Br | H | H | 210–214 | 48.47 | 3.11 | 6.65 |
|  |  |  |  |  |  |  | 48.63 | 3.31 | 6.58 |
| 107 | 94 | SO₂ | CH₂CH₃ | H | H | 216–220 (EtOH) | 51.42 | 4.31 | 9.99 |
|  |  |  |  |  |  |  | 51.40 | 4.10 | 10.07 |
| 108 | 95 | SO₂ | (CH₂)₃CH₃ | H | H | 215–218 (EtOH) | 54.53 | 5.23 | 9.08 |
|  |  |  |  |  |  |  | 54.48 | 4.84 | 9.13 |
| 109 | 96 | SO₂ | CH₂-C₆H₄-F | H | H | 203–205 | 56.66 | 3.64 | 7.77 |
|  |  |  |  |  |  |  | 56.41 | 3.81 | 7.70 |
| 110 | 97 | SO₂ | CH₂-C₆H₃(F)-Cl | H | H | 267–270 | 51.72 | 3.06 | 7.09 |
|  |  |  |  |  |  |  | 51.72 | 3.19 | 6.97 |
| 111 | 98 | SO₂ | CH(CH₃)₂ | H | H | 217–220 | 53.05 | 4.79 | 9.52 |
|  |  |  |  |  |  |  | 52.90 | 4.91 | 9.21 |

-continued

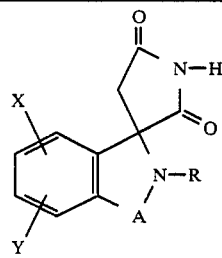
(I)

| Example | Example of Starting Material | A | R | X | Y | m.p. °C. | Analysis % Calcd.(upper) Found(lower) | | |
|---|---|---|---|---|---|---|---|---|---|
| | | | | | | | C | H | N |
| 112 | 99 | SO₂ | CH₂-(1-Br-naphthyl) | H | H | 250–252 | 53.51 / 53.32 | 3.21 / 3.34 | 5.94 / 5.62 |
| 113 | 100 | SO₂ | CH₂-(2-naphthyl) | H | H | 135–155 (calcd. for C₂₁H₁₆N₂O₄S.¼ H₂O) 63.30 | 63.54 / 4.31 | 4.20 / 6.94 | 7.06 |
| 114 | 47 | CO | CH₂Ph | H | H | 222–225 | 70.58 / 70.48 | 4.61 / 4.78 | 9.14 / 9.03 |
| 115 | 48 | CO | CH₂-(3,4-diCl-phenyl) | H | H | 207–209 | 60.26 / 60.08 | 3.37 / 3.55 | 7.81 / 7.76 |
| 116 | 49 | CO | CH₂-(4-Br-2-F-phenyl) | H | H | 230–237 (EtOH) | 53.62 / 53.52 | 3.00 / 2.94 | 6.95 / 7.04 |
| 117 | 50 | CO | CH₃ | H | H | 298–302 (EtOH) | 62.60 / 62.49 | 4.38 / 4.34 | 12.17 / 12.14 |
| 118 | 51 | CO | CH₂-(2-F-6-Cl-phenyl) | H | H | 207–209 | 60.26 / 60.08 | 3.37 / 3.55 | 7.81 / 7.76 |
| 119 | 52 | CO | (CH₂)₃CH₃ | H | H | 182–186 | 66.16 / 66.10 | 5.92 / 5.86 | 10.20 / 10.21 |
| 120 | 53 | CO | CH₃ | 5-Cl | H | 318–329 (dec.) | 54.46 / 54.51 | 3.43 / 3.07 | 10.58 / 10.58 |
| 121 | 54 | CO | CH₂-(4-Br-2-F-phenyl) | 6-Cl | H | 218–222 | 49.40 / 49.47 | 2.53 / 2.41 | 6.40 / 6.24 |
| 122 | 55 | CO | CH₃ | 5-Cl | 6-Cl | 289–293 | 48.19 / 48.31 | 2.70 / 2.90 | 9.37 / 8.98 |
| 123 | 56 | CO | CH₃ | 6-F | H | 322–326 (dec.) | 58.07 / 58.16 | 3.65 / 4.01 | 11.29 / 11.10 |
| 124 | 57 | CO | CH₃ | 5,6-CH=CH—CH=CH | | 295–297 | 68.57 / 68.38 | 4.32 / 4.35 | 9.99 / 10.36 |
| 125 | 58 | CO | CH₃ | 7-Cl | H | 310–311 | 54.46 / 54.26 | 3.43 / 3.49 | 10.58 / 10.31 |
| 126 | 59 | CO | CH₃ | 4-Cl | H | 352–356 | 54.46 | 3.43 | 10.59 |

-continued

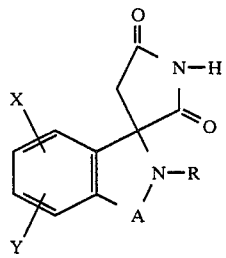

| Example | Example of Starting Material | A | R | X | Y | m.p. °C. | Analysis % Calcd.(upper) Found(lower) C | H | N |
|---|---|---|---|---|---|---|---|---|---|
| 127 | 60 | CO | $CH_3$ | 5-Br | H | (dec.) 316–322 | 54.32 46.63 46.29 | 3.43 2.85 3.05 | 10.55 8.80 8.47 |
| 128 | 61 | CO | $CH_2CH_3$ | 6-Cl | H | 297–298 (dec.) | 56.03 56.11 | 3.98 4.04 | 10.05 9.81 |
| 129 | 62 | CO | $CH_3$ | 5-$OCH_3$ | H | 226–232 (EtOH) | 60.00 59.60 | 4.65 4.79 | 10.76 10.59 |
| 130 | 63 | CO | $CH_3$ | 5-$SCH_3$ | H | 243–253 (EtOH) | 56.51 56.20 | 4.38 4.44 | 10.14 9.83 |
| 131 | 64 | CO | $CH_2CH_2CH_3$ | 5-Cl | 6-Cl | 247–250 | 51.40 51.32 | 3.70 3.54 | 8.56 8.49 |
| 132 | 65 | CO | $CH_3$ | 6-$NO_2$ | H | 357(dec.) | 52.37 52.00 | 3.30 3.35 | 15.27 15.19 |
| 133 | 66 | CO | $CH_3$ | 5-$CH_3$ | H | 276–283 | 63.93 63.60 | 4.95 5.12 | 11.47 11.37 |
| 134 | 67 | CO | $CH_3$ | 6-$CO_2CH_3$ | H | 273–278 (calcd. for $C_{14}H_{12}N_2O_5 \cdot 1/12\ H_2O$) 57.86 | 58.03 4.05 | 4.24 | 9.67 9.38 |
| 135 | 68 | CO | $CH_3$ | 4-$CH_3$ | H | 327–329 (dec.) | 63.93 63.73 | 4.95 4.88 | 11.47 11.10 |
| 136 | 69 | CO | $CH_3$ | 5-Ph | H | 273–275 | 70.58 70.18 | 4.61 4.55 | 9.14 8.90 |

We claim:
1. A compound of formula (I)

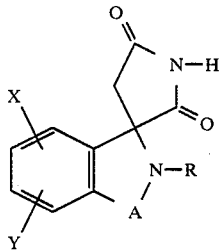

wherein A is CO; R is lower alkyl containing 1 to 6 carbon atoms, benzyl, halogen substituted benzyl, (2-naphthalenyl)methyl, (1-bromo-2-naphthalenyl)methyl; X is hydrogen, halogen, lower alkyl containing 1 to 4 carbon atoms, lower alkoxy containing 1 to 4 carbon atoms, lower alkylthio containing 1 to 4 carbon atoms, carboalkoxy containing 1 to 4 carbon atoms, phenyl, nitro; Y is hydrogen or chlorine; or X and Y are joined to form CH=CH—CH=CH, and the pharmaceutically acceptable salts thereof.

2. The compounds according to claim 1 of formula (III)

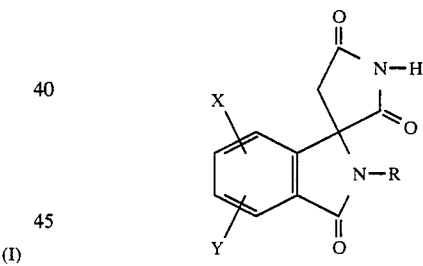

wherein R is lower alkyl containing 1 to 4 carbon atoms, benzyl, halogen substituted benzyl; X is hydrogen, lower alkyl containing 1 to 4 carbon atoms, lower alkoxy containing 1 to 4 carbon atoms, lower alkylthio containing 1 to 4 carbon atoms, carboalkoxy containing 1 to 4 carbon atoms, phenyl, nitro; Y is hydrogen or chlorine; or X and Y are joined to form CH=CH—CH=CH, and the pharmaceutically acceptable salts thereof.

3. The compounds according to claim 2 of formula (III) wherein R is halogen substituted benzyl, X and Y are hydrogens; or R is lower alkyl containing 1 to 2 carbon atoms, Y is hydrogen and X is halogen or lower alkyl containing 1 to 3 carbon atoms or 5- phenyl; or R is lower alkyl containing 1 to 2 carbon atoms, X is 5—Cl and Y is 6—Cl; or R is lower alkyl containing 1 to 2 carbon atoms, X and Y are joined to form 5, 6—CH=CH—CH=CH, and the pharmaceutically acceptable salts thereof.

4. The compound according to claim 3, formula (III) designated 6-chloro-2-methylspiro[1H-isoindole-1,3'- pyrrolidine]-2',3,5'(2H)-trione, and the pharmaceutically acceptable salts thereof.

5. The compound according to claim 3, formula (III) designated 5,6-dichloro-2-methylspiro[1H-isoindole-1,3'-pyrrolidine]-2',3,5'(2H)-trione, and the pharmaceutically acceptable salts thereof.

6. The compound according to claim 3, formula (III) designated 5-chloro-2-methylspiro[1H-isoindole-1,3'-pyrrolidine]-2',3,5'(2H)-trione, and the pharmaceutically acceptable salts thereof.

7. The compound according to claim 3, formula (III) designated 2,4-dimethylspiro[1H-isoindole-1,3'-pyrrolidine]-2',3,5'(2H)-trione, and the pharmaceutically acceptable salts thereof.

8. The compound according to claim 3, formula (II) designated 2-[(4-bromophenyl)methyl]-2,3-dihydrospiro[1,2-benzisothiazole-3,3'-pyrrolidine]-2',5'-dione 1,1-dioxide, and the pharmaceutically acceptable salts thereof.

9. The compound according to claim 3, formula (III) designated 2-[(4-bromo-2-fluorophenyl)methyl]-spiro[1H-isoindole-1,3'-pyrrolidine]-2',3,5'(2H)-trione, and the pharmaceutically acceptable salts thereof.

10. A pharmaceutical composition for preventing or relieving neuropathy, nephropathy, retinopathy, or cataracts in a diabetic mammal, which comprises an alleviating or prophylactic amount of a compound of claim 1 and a pharmaceutically acceptable carrier.

11. A pharmaceutical composition for preventing or relieving hyperglycemia in a diabetic mammal, which comprises an alleviating or prophylactic amount of a compound of claim 1 and a pharmaceutically acceptable carrier.

12. A method of preventing or relieving neuropathy, nephropathy, retinopathy, or cataracts in a diabetic mammal, which comprises administering to said mammal an alleviating or prophylactic amount of a compound of claim 1.

13. A method of preventing or relieving hyperglycemia in a diabetic mammal, which comprises administering to said mammal an alleviating or prophylactic amount of a compound of claim 1.

* * * * *